(12) United States Patent  
Xu

(10) Patent No.: US 10,485,456 B2  
(45) Date of Patent: Nov. 26, 2019

(54) IDENTIFICATION METHOD AND DEVICE

(71) Applicant: Beijing Zhigu Rui Tuo Tech Co., Ltd, Beijing (CN)

(72) Inventor: Ran Xu, Beijing (CN)

(73) Assignee: BEIJING ZHIGU RUI TUO TECH CO., LTD, Beijing (CN)

( * ) Notice: Subject to any disclaimer, the term of this patent is extended or adjusted under 35 U.S.C. 154(b) by 6 days.

(21) Appl. No.: 15/307,798

(22) PCT Filed: Apr. 16, 2015

(86) PCT No.: PCT/CN2015/076714  
§ 371 (c)(1),  
(2) Date: Oct. 28, 2016

(87) PCT Pub. No.: WO2015/165332  
PCT Pub. Date: Nov. 5, 2015

(65) Prior Publication Data  
US 2017/0049364 A1    Feb. 23, 2017

(30) Foreign Application Priority Data

Apr. 30, 2014  (CN) .......................... 2014 1 0179083

(51) Int. Cl.  
*A61B 5/117*  (2016.01)  
*A61B 5/02*   (2006.01)  
(Continued)

(52) U.S. Cl.  
CPC ................ *A61B 5/117* (2013.01); *A61B 5/02* (2013.01); *A61B 5/026* (2013.01);  
(Continued)

(58) Field of Classification Search  
CPC .......... G06F 3/011; G06F 3/014; G06F 3/015; G06F 3/017; A61B 5/117; A61B 5/02; A61B 5/02055; A61B 5/026  
See application file for complete search history.

(56) References Cited

U.S. PATENT DOCUMENTS 5,865,756 A * 2/1999 Peel, III ............. A61B 5/02116  
600/485  
8,147,416 B2 * 4/2012 Fayram ................ A61B 5/0215  
600/481  
(Continued)

FOREIGN PATENT DOCUMENTS

CN   101647702 A   2/2010  
CN   102449573 A   5/2012  
(Continued)

OTHER PUBLICATIONS

International Search Report for PCT Application No. PCT/CN2015/076714, dated Jul. 20, 2015, 4 pages.

*Primary Examiner* — Sejoon Ahn  
(74) *Attorney, Agent, or Firm* — Amin, Turocy & Watson, LLP

(57) ABSTRACT

This application provides an identification method and device, and relates to the field of wearable devices. The method comprises: acquiring a first heartbeat propagation signal and a second heartbeat propagation signal separately from a target limb of a body; and identifying whether the target limb is a left limb or a right limb at least according to the first heartbeat propagation signal and the second heartbeat propagation signal. The method and device can implement automatic identification of left and right limbs, simplify configuration steps, and improve user experience.

29 Claims, 9 Drawing Sheets

(51) Int. Cl.
- *A61B 5/00* (2006.01)
- *G06F 3/01* (2006.01)
- *A61B 5/0456* (2006.01)
- *A61B 5/11* (2006.01)
- *A61B 5/0205* (2006.01)
- *A61B 5/026* (2006.01)
- *A61B 5/0402* (2006.01)
- *A61B 5/0295* (2006.01)
- *A61B 5/021* (2006.01)

(52) U.S. Cl.
CPC ........ *A61B 5/02055* (2013.01); *A61B 5/0402* (2013.01); *A61B 5/0456* (2013.01); *A61B 5/1114* (2013.01); *A61B 5/1123* (2013.01); *A61B 5/681* (2013.01); *G06F 3/011* (2013.01); *G06F 3/014* (2013.01); *G06F 3/015* (2013.01); *G06F 3/017* (2013.01); *A61B 5/02028* (2013.01); *A61B 5/0261* (2013.01); *A61B 5/0295* (2013.01); *A61B 5/02125* (2013.01); *A61B 5/1107* (2013.01); *A61B 5/1121* (2013.01); *A61B 5/7285* (2013.01); *A61B 2503/10* (2013.01); *A61B 2505/09* (2013.01); *A61B 2560/0223* (2013.01); *A61B 2560/0462* (2013.01); *A61B 2562/06* (2013.01)

(56) References Cited

U.S. PATENT DOCUMENTS

| | | | | |
|---|---|---|---|---|
| 8,162,841 | B2* | 4/2012 | Keel | A61B 5/02158 600/481 |
| 8,419,649 | B2* | 4/2013 | Banet | A61B 5/02125 600/493 |
| 8,467,860 | B2* | 6/2013 | Salazar | A61B 5/0006 600/301 |
| 2003/0139675 | A1* | 7/2003 | Ogura | A61B 5/0205 600/492 |
| 2007/0276632 | A1 | 11/2007 | Banet et al. | |
| 2009/0024004 | A1 | 1/2009 | Yang | |
| 2009/0295743 | A1* | 12/2009 | Nakajoh | G06F 3/04883 345/173 |
| 2010/0094277 | A1* | 4/2010 | Sato | A61B 18/1492 606/41 |
| 2010/0310136 | A1 | 12/2010 | Tsuda | |
| 2012/0095353 | A1* | 4/2012 | Mori | A61B 5/02007 600/500 |
| 2013/0150743 | A1* | 6/2013 | Tomimori | A61B 5/0456 600/521 |
| 2013/0267859 | A1* | 10/2013 | Okuda | A61B 5/0245 600/500 |
| 2013/0271360 | A1* | 10/2013 | MacDougall | H04M 1/72519 345/156 |
| 2013/0324848 | A1* | 12/2013 | Kuroki | A61B 5/021 600/438 |
| 2014/0006496 | A1 | 1/2014 | Dearman et al. | |
| 2014/0221849 | A1* | 8/2014 | Farringdon | A61B 5/0428 600/483 |
| 2014/0267084 | A1* | 9/2014 | Krulce | G06F 3/0416 345/173 |
| 2014/0275852 | A1* | 9/2014 | Hong | A61B 5/02427 600/301 |
| 2014/0276149 | A1* | 9/2014 | Takahashi | A61B 5/02438 600/503 |
| 2016/0128895 | A1* | 5/2016 | Kobayashi | A61H 9/0078 601/150 |
| 2016/0287172 | A1* | 10/2016 | Morris | A61B 5/04085 |
| 2018/0043246 | A1* | 2/2018 | Chang | A63F 13/213 |
| 2018/0192946 | A1* | 7/2018 | Adachi | A61B 5/022 |

FOREIGN PATENT DOCUMENTS

| | | |
|---|---|---|
| CN | 102860822 A | 1/2013 |
| CN | 103271732 A | 9/2013 |
| CN | 103393414 A | 11/2013 |
| CN | 103744531 A | 4/2014 |
| CN | 103941873 A | 7/2014 |
| JP | 2004129979 A | 4/2004 |

* cited by examiner right hand unlock      left hand unlock

IDENTIFICATION METHOD AND DEVICE

RELATED APPLICATION

The present application is a U.S. National Stage filing under 35 U.S.C. § 371 of international patent cooperation treaty (PCT) application No. PCT/CN2015/076714, filed Apr. 16, 2015, and entitled "IDENTIFICATION METHOD AND DEVICE", which claims the benefit of priority to Chinese Patent Application No. 201410179083.5, filed on Apr. 30, 2014, which applications are hereby incorporated into the present application by reference herein in their respective entireties.

TECHNICAL FIELD

This application relates to the field of wearable device technologies, and in particular, to an identification method and device.

BACKGROUND

Along with the development of electronic devices, wearable devices such as smart wrist bands and smart watches are gradually popularized. People can use the wearable devices conveniently to monitor the amount of exercise, monitor sleep quality, monitor health conditions, view mobile phone information, and the like.

Generally, existing wearable devices such as smart wrist bands and smart watches request that a user preset a wearing part for purposes of ensuring monitoring precision and facilitating user operations. For example, each time a user wears a smart wrist band, the smart wrist band prompts the user to input information about whether a current wearing part is a left hand or a right hand, so as to complete corresponding wearing setting. The configuration process increases the operation time of the user, and deteriorates user experience.

SUMMARY

This application is directed to: providing an identification method and device.

According to one example aspect of at least one embodiment of this application, an identification method is provided, the method comprising:

acquiring a first heartbeat propagation signal and a second heartbeat propagation signal separately from a target limb of a body; and identifying whether the target limb is a left limb or a right limb at least according to the first heartbeat propagation signal and the second heartbeat propagation signal.

According to another example aspect of at least one embodiment of this application, an identification device is provided, the device comprising:

an acquiring module, configured to acquire a first heartbeat propagation signal and a second heartbeat propagation signal separately from a target limb of a body; and an identification module, configured to identify whether the target limb is a left limb or a right limb at least according to the first heartbeat propagation signal and the second heartbeat propagation signal.

In the example methods and devices according to the embodiments of this application, the first heartbeat propagation signal and the second heartbeat propagation signal are acquired from the target limb, and whether the target limb is a left limb or a right limb is identified at least according to the first heartbeat propagation signal and the second heartbeat propagation signal, thereby implementing automatic identification of left and right limbs, simplifying configuration steps, and improving user experience.

DETAILED DESCRIPTION

Example embodiments of this application are further described below in detail with reference to accompanying drawings and embodiments. The following embodiments are used to describe this application, but are not intended to limit the scope of this application.

A person skilled in the art should understand that in the embodiments of this application, the value of the sequence number of each step does not indicate an execution order, and the execution order of the steps should be determined according to a function and an inherent logic thereof, and should not form any limit to the implementation process of the embodiments of this application.

It is noted that existing wearable devices, such as a smart watch and a smart wrist band, generally all have a capability of detecting an electrocardiographic waveform signal and a blood flow pulsation waveform signal. Meanwhile, it is assumed that a difference between a time in which an electrocardiographic waveform signal corresponding to a cardiac cycle reaches the left hand and a time in which a blood flow pulsation waveform signal corresponding to the cardiac cycle reaches the left hand is $\Delta T_L$, and a difference between a time in which the electrocardiographic waveform signal corresponding to the cardiac cycle reaches the right hand and a time in which the blood flow pulsation waveform signal corresponding to the cardiac cycle reaches the right hand is $\Delta T_R$. Since the heart is asymmetrical (that is, located on the left of the chest) in the human body, there is an obvious difference between $\Delta T_L$ and $\Delta T_R$ (a reason for this difference will be explained in detail later). This application implements identification of left and right hands based on this difference, and similarly implements identification of left and right arms, left and right shoulders, left and right feet, and left and right legs.

Figure 1:
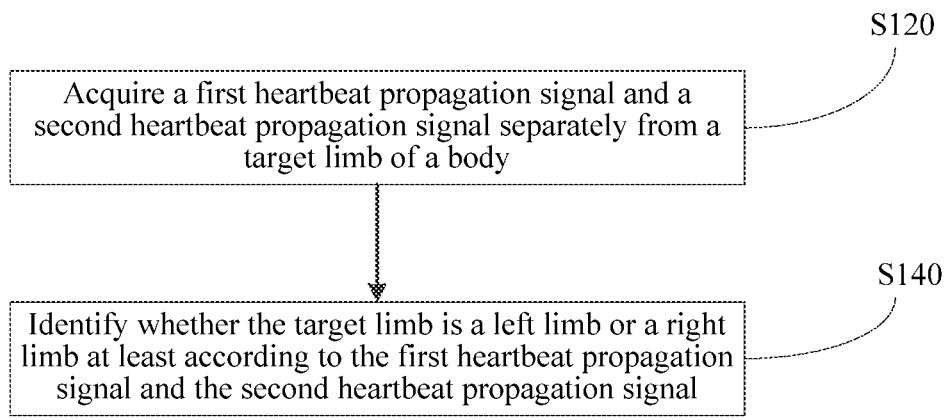
FIG. 1 is an example flowchart of an identification method according to an embodiment of this application.

FIG. 1 is a flowchart of an identification method according to an embodiment of this application, and the identification method may be implemented in, for example, an identification device. As shown in FIG. 1, the method comprises:

S120: Acquire a first heartbeat propagation signal and a second heartbeat propagation signal separately from a target limb of a body.

S140: Identify whether the target limb is a left limb or a right limb at least according to the first heartbeat propagation signal and the second heartbeat propagation signal.

In the method according to the embodiment of this application, the first heartbeat propagation signal and the second heartbeat propagation signal are acquired from the target limb, and whether the target limb is a left limb or a right limb is identified at least according to the first heartbeat propagation signal and the second heartbeat propagation signal, thereby implementing automatic identification of left and right limbs, simplifying configuration steps, and improving user experience.

Functions of steps S120 and S140 are described below in detail with reference to example embodiments.

S120: Acquire a first heartbeat propagation signal and a second heartbeat propagation signal separately from a target limb of a body.

The target limb is one of a left limb and a right limb described later, which may be a hand, an arm, a shoulder, a foot, or a leg. In addition, the identification of the target limb in this application comprises: identifying the left hand or right hand from two hands of a human body, identifying the left arm or right arm from two arms of a human body, identifying the left shoulder or right shoulder from two shoulders of a human body, identifying the left foot or right foot from two feet of a human body, or identifying the left leg or right leg from two legs of a human body. A person skilled in the art should understand that identification principles for hands, arms, shoulders, feet or legs are the same, and identification processes for hands, arms, shoulders, feet or legs are similar; therefore, for the sake of simplicity, this application emphasizes identifying the left hand or right hand from two hands of the human body.

The first heartbeat propagation signal and the second heartbeat propagation signal are heartbeat propagation signals of different types, in other words, the first heartbeat propagation signal and the second heartbeat propagation signal are two heartbeat propagation signals having different propagation speeds in the human body. For example, the first heartbeat propagation signal may be one of an electrocardiographic waveform signal and a blood flow pulsation waveform signal, and the second heartbeat propagation signal may be one of the electrocardiographic waveform signal and the blood flow pulsation waveform signal different from the first heartbeat propagation signal. The electrocardiographic waveform signal is a signal reflecting electrical activities generated by the heart during every cardiac cycle, and may be, for example, an electrocardiogram of the human body, which may be obtained by using, for example, a group of ECG detecting motor. The blood flow pulsation waveform signal is a signal reflecting blood flow pulsation generated by the heart during every cardiac cycle, which may be, for example, a photoplethysmography (PPG) pulse wave of the human body, which may be obtained by using, for example, an optical sensor, an ultrasonic sensor, an electromagnetic field sensor, or the like.

S140: Identify whether the target limb is a left limb or a right limb at least according to the first heartbeat propagation signal and the second heartbeat propagation signal.

In an example embodiment, step S140 may comprise:

S141: Acquire a time corresponding to a first feature point on the first heartbeat propagation signal;

S142: Acquire a time corresponding to a second feature point on the second heartbeat propagation signal, the second feature point being corresponding to the first feature point; and S143: Identify whether the target limb is a left limb or a right limb at least according to a time difference between the time corresponding to the first feature point and the time corresponding to the second feature point.

The first feature point may be a crest on the first heartbeat propagation signal, and correspondingly the second feature point may be a crest on the second heartbeat propagation signal. Certainly, a person skilled in the art should understand that the first feature point may further be a trough on the first heartbeat propagation signal, and correspondingly, the second feature point may further be a trough on the second heartbeat propagation signal; or, the first feature point may further be a crest on the first heartbeat propagation signal, and correspondingly, the second feature point may further be a trough on the second heartbeat propagation signal; or the first feature point may further be a trough on the first heartbeat propagation signal, and correspondingly, the second feature point may further be a crest on the second heartbeat propagation signal. For the sake of simplicity, description is made below only by using an example in which the first feature point and the second feature point are respectively crests on corresponding heartbeat propagation signals.

Selection of the first feature point and the second feature point may be determined according to a propagation speed relationship between the first heartbeat propagation signal and the second heartbeat propagation signal. For example, generally, the electrocardiographic waveform signal having a high propagation speed may be used as the first heartbeat propagation signal, and the blood flow pulsation waveform signal having a low propagation speed may be used as the second heartbeat propagation signal; in this way, a crest may be selected randomly on the electrocardiographic waveform signal to serve as the first feature point, and correspondingly, an nth crest after the first feature point may be selected on the blood flow pulsation waveform signal to serve as the second feature point, where n is a preset value. The preset value may be set in advance, for example, may be 1, 2, or the like. Meanwhile, in consideration of reducing the error, the first feature point and the second feature point are preferably located in a same cardiac cycle, that is, the preset value is 1.

In an example embodiment, step S143 may comprise:

S143a: Identify whether the target limb is a left limb or a right limb according to a reference time difference and a time difference between the time corresponding to the first feature point and the time corresponding to the second feature point.

Figure 2:
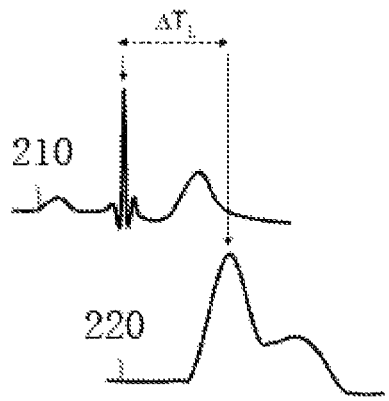
FIG. 2 shows a time difference between a crest on an electrocardiographic waveform signal and a crest on a blood flow pulsation waveform signal measured at a left wrist according to an example embodiment of this application.

Referring to FIG. 2, the waveform at the upper part is a waveform graph of an electrocardiographic waveform signal 210 measured at the left wrist of the human body, the waveform at the lower part is a waveform graph of a blood flow pulsation waveform signal 220 measured at the left wrist of the human body, and it can be seen that, in a same cardiac cycle, the crest on the electrocardiographic waveform signal 210 measured at the left wrist reaches the left wrist first, then the crest on the blood flow pulsation waveform signal 220 measured at the left wrist reaches the left wrist, and a time difference $\Delta T_L$ exists between the two crests, which may be recorded as a left hand time difference. The reason for the time difference lies in that the propagation speed of the electrocardiographic waveform signal in the human body is greater than that of the blood flow pulsation waveform signal.

Figure 3:
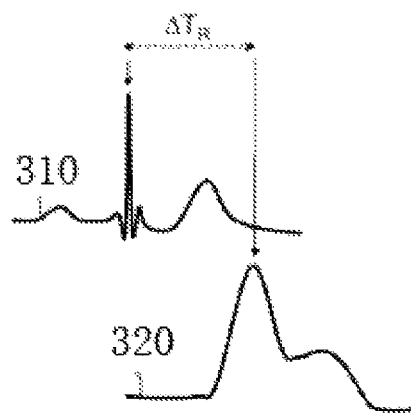
FIG. 3 shows a time difference between a crest on an electrocardiographic waveform signal and a crest on a blood flow pulsation waveform signal measured at a right wrist according to an example embodiment of this application.

Referring to FIG. 3, the waveform at the upper part is a waveform graph of an electrocardiographic waveform signal 310 measured at the right wrist of the human body, the waveform at the lower part is a waveform graph of a blood flow pulsation waveform signal 320 measured at the right wrist of the human body, and similarly, since the propagation speed of the electrocardiographic waveform signal in the human body is greater than that of the blood flow pulsation waveform signal, the crest on the electrocardiographic waveform signal 310 measured at the right wrist reaches the right wrist first, then the crest on the blood flow pulsation waveform signal 320 measured at the right wrist reaches the right wrist, and a time difference $\Delta T_R$ exists between the two crests, which may be recorded as a right hand time difference.

Figure 4:
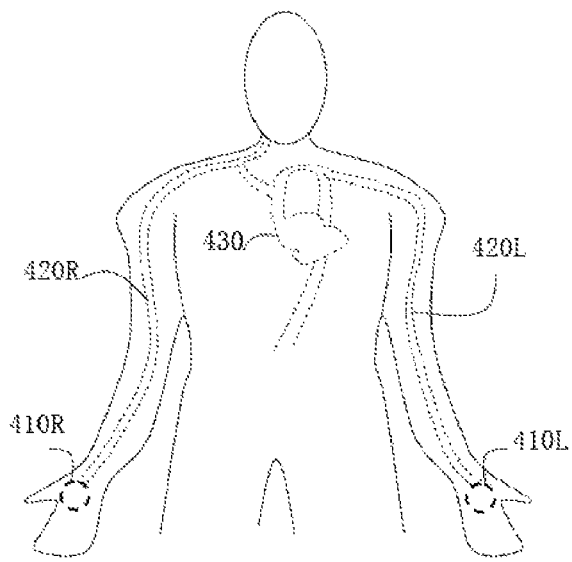
FIG. 4 is an example asymmetric schematic diagram of a heart according to an example embodiment of this application.

During research, the inventor finds that the left hand time difference $\Delta T_L$ is obviously less than the right hand time difference $\Delta T_R$ because of the asymmetry of the heart of the human body. Referring to FIG. 4, a transmission path of a signal (comprising a blood flow pulsation waveform signal and an electrocardiographic waveform signal) from a heart 430 to a left wrist 410L is a left side path 420L, and a distance thereof is assumed as $D_L$; and a transmission path of the signal from the heart 430 to a right wrist 410R is a right side path 420R, and a distance thereof is assumed as $D_R$. The heart 430 is located on the left of the chest, and therefore, $D_L<D_R$. It may be assumed that a propagation speed of the blood flow pulsation waveform signal is $V_P$, and a propagation speed of the electrocardiographic waveform signal is $V_E$, and then:

$$\Delta T_L = \frac{D_L}{V_P} - \frac{D_L}{V_E} = D_L \times \left(\frac{1}{V_P} - \frac{1}{V_E}\right), \quad (1)$$

and $$\Delta T_R = \frac{D_R}{V_P} - \frac{D_R}{V_E} = D_R \times \left(\frac{1}{V_P} - \frac{1}{V_E}\right) \quad (2)$$

According to the above formulas (1) and (2), and $D_L<D_R$, it may be derived that $\Delta T_L<T_R$.

Therefore, in an example embodiment, the reference time difference may be determined in advance, and the reference time difference may comprise a left-hand reference time difference and a right-hand reference time difference, and the left-hand reference time difference $\Delta T_{CL}$ and the right-hand reference time difference $\Delta T_{CR}$ may be obtained through experiments. In step S123, a time difference between the time corresponding to the first feature point and the time corresponding to the second feature point (denoted as an actually measured time difference in brief below) is compared with the left-hand reference time difference $\Delta T_{CL}$ and the right-hand reference time difference $\Delta T_{CR}$ to determine whether they are matched, thereby determining whether the target limb is the left hand or the right hand. Specifically, the left-hand reference time difference $\Delta T_{CL}$ may be a first time value, the right-hand reference time difference $\Delta T_{CR}$ may be a second time value, and identification may be implemented according to proximities of the actually measured time difference to the two time values. For example, when the actually measured time difference is closer to the first time value, it may be determined that the target limb is the left hand. Or, as shown in Table 1, the left-hand reference time difference $\Delta T_{CL}$ may be in a first time interval (0.27 s, 0.29 s), the right-hand reference time difference $\Delta T_{CR}$ may be in a second time interval (0.37 s, 0.39 s), and identification may be implemented according to situations in which the actually measured time difference falls within the two time intervals. For example, when the actually measured time difference is 0.275 s which falls within the first time interval, it may be determined that the target limb is the left hand.

TABLE 1

| $\Delta T_{CL}$ | $\Delta T_{CR}$ |
| --- | --- |
| (0.27 s, 0.29 s) | (0.37 s, 0.39 s) |

In addition, in another example embodiment, the reference time difference may also merely comprise one of the left-hand reference time difference and the right-hand reference time difference. For example, the reference time difference merely comprises the left-hand reference time difference $\Delta T_{CL}$, which is in a time interval; it may be determined whether the actually measured time difference falls within the time interval, and if yes, the target limb is the left hand; otherwise, the target limb is the right hand.

Figure 5:
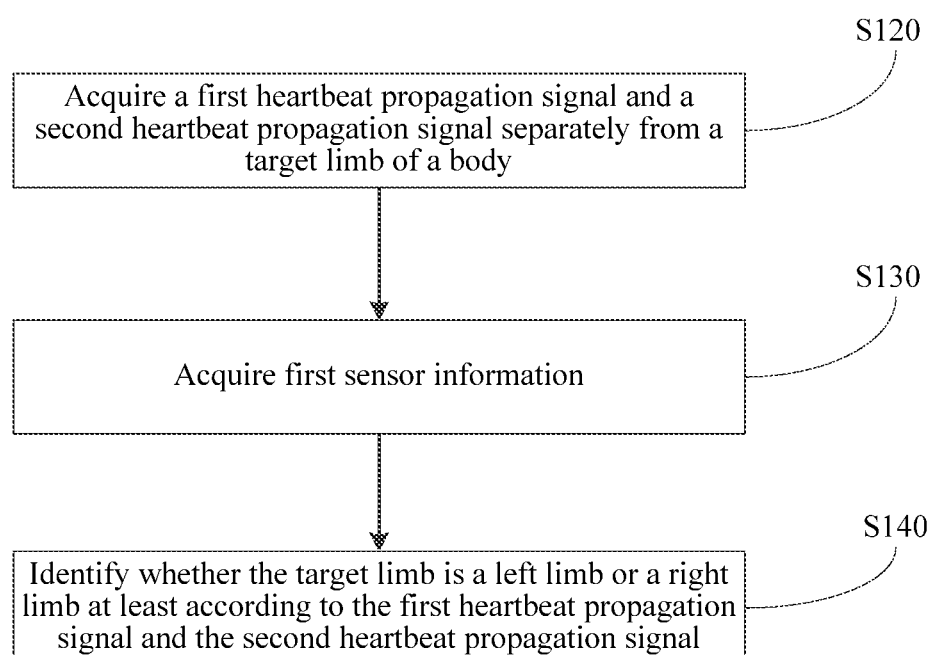
FIG. 5 is an example flowchart of an identification method according to an example embodiment of this application.

Meanwhile, during research, the inventor further finds that the pulse, blood pressure, body temperature, motion state, body gesture, and the like of the human body will affect the result of the actually measured time difference. For example, when the human body is in a motion state, the propagation speed of the blood flow pulsation waveform signal is increased, while the propagation speed of the electrocardiographic waveform signal is almost unaffected; in this case, the actually measured time difference is less than that in a non-motion state. For another example, when the target limb under detection is in a raised state (for example, the right hand is raised), the propagation speed of the blood flow pulsation waveform signal is lowered due to the gravity, while the propagation speed of the electrocardiographic waveform signal is almost unaffected; in this case, the actually measured time difference is greater than that in a non-raised state. Therefore, in order to improve the identification precision, referring to FIG. 5, in an example embodiment, the method further comprises:

S130: Acquire first sensor information.

The first sensor information comprises: at least one of pulse information, blood pressure information, body temperature information, motion state information, and body gesture information.

Moreover, step S143 may comprise:

S143b: Identify whether the target limb is a left limb or a right limb according to a reference time difference, the first sensor information, and a time difference between the time corresponding to the first feature point and the time corresponding to the second feature point.

Assuming that the first sensor information is the pulse information, which is specifically the number of pulses per minute, the reference time difference may be shown as that in Table 2. Corresponding to different pulse information, corresponding reference time differences have slight differences. For example, when the user is in motion, the number of pulses per minute is in [90, 100], a left-hand reference time difference $\Delta T_{CL}$ is in (0.268 s, 0.272 s], and some data thereof does not fall within the range of the left-hand reference time difference (0.268 s, 0.272 s) in a non-motion state. Assuming that the detection result displays that the current pulse information of the user is 100 per minute, and the actually measured time difference is 0.269 s, it may be determined that the target limb is the left hand.

TABLE 2

| Pulse information | $\Delta T_{CL}$ | $\Delta T_{CR}$ |
|---|---|---|
| [60, 70) | (0.286 s, 0.290 s] | (0.386 s, 0.390 s] |
| [70, 80) | (0.276 s, 0.286 s] | (0.376 s, 0.386 s] |
| [80, 90) | (0.272 s, 0.276 s] | (0.372 s, 0.376 s] |
| [90, 100] | (0.268 s, 0.272 s] | (0.368 s, 0.372 s] |

Figure 6:
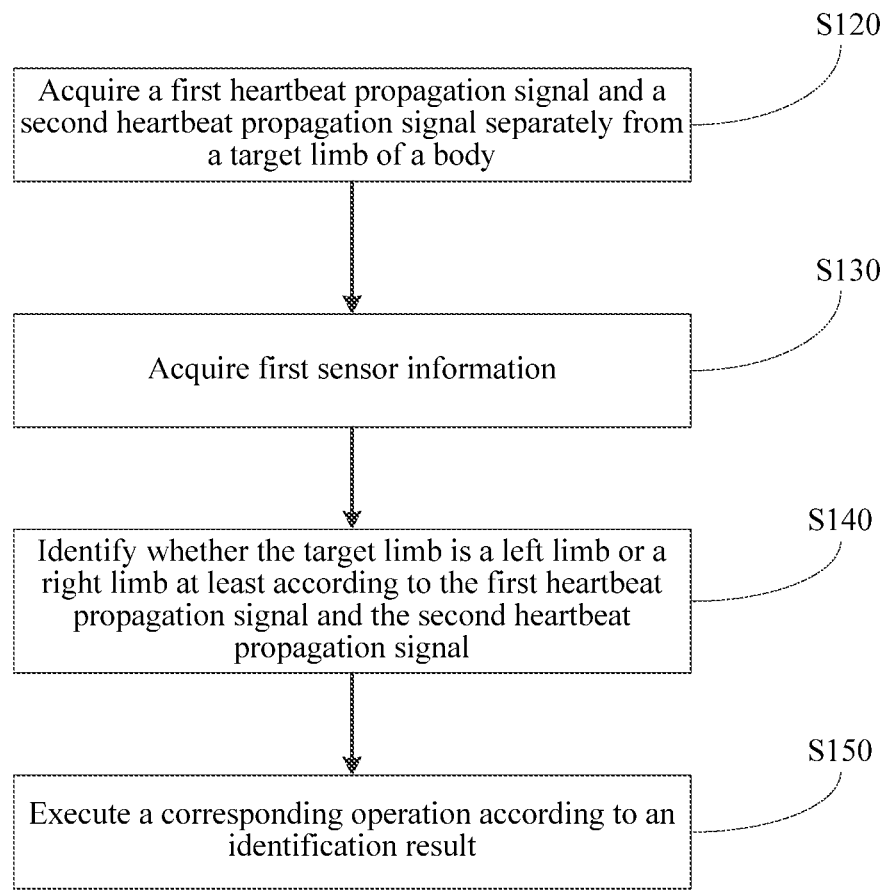
FIG. 6 is an example flowchart of an identification method according to another example embodiment of this application.

As shown in FIG. 6, in an example embodiment of this application, the method may further comprise:

S150: Execute a corresponding operation according to an identification result.

The executing a corresponding operation may comprise: at least one of mode switching, user prompting, and device matching. For example, if the user transfers a wrist band (comprising an identification device) from the right hand to the left hand, and the identification device automatically identifies that the wrist band is worn on the left hand, a right hand mode is switched to a left hand mode, and the identification device can prompt the user that currently the right hand mode is switched to the left hand mode. In addition, a smartphone may be notified to establish a matching relationship with the wrist band based on the left hand mode.

Figure 7:
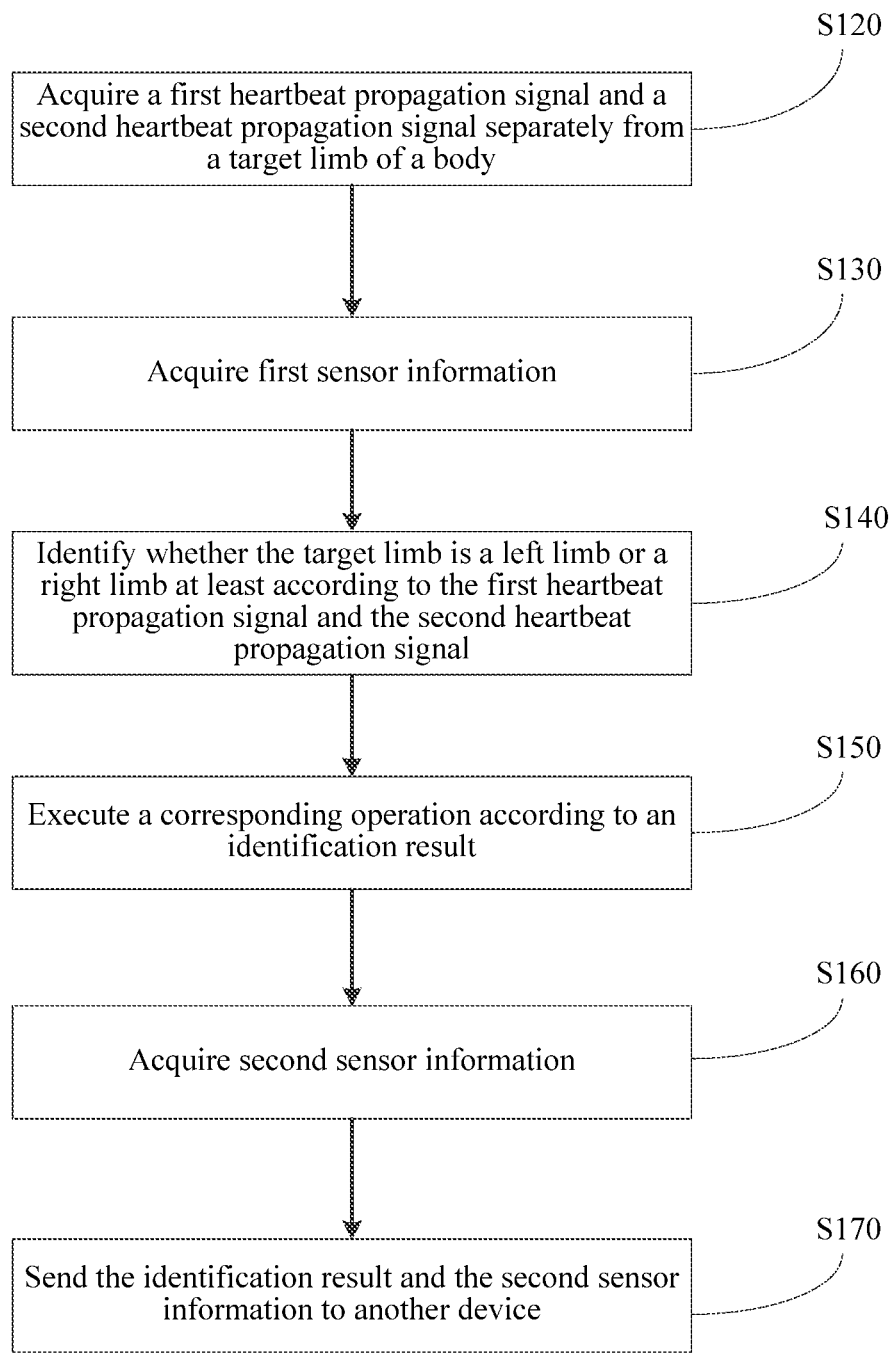
FIG. 7 is an example flowchart of an identification method according to another example embodiment of this application.

In addition, during research, the inventor finds that the identification result, in combination with some sensor data, may further assist another device in determining whether the another device is located on the left hand or the right hand of the user. For example, in response to the identification device worn on the left hand of the user, a smartphone is held by the left hand of the user at the same time, the identification device and the smartphone can collect the same acceleration data. Therefore, as shown in FIG. 7, in an example embodiment of this application, the method further comprises:

S160: Acquire second sensor information.

S170: Send the identification result and the second sensor information to another device.

The second sensor information may comprise acceleration information, angle information, and the like. In addition, the other device may compare the second sensor information with sensor information of the other device, and may determine, according to a comparison result, a part of the body of the user where the other device is located. For example, assuming that the identification result displays that the target limb is the left hand, and meanwhile, the second sensor information is consistent with the sensor information of the another device, the another device is also located at the left hand of the user; assuming that the identification result displays that the target limb is the right hand, and meanwhile, the second sensor information is consistent with the sensor information of the another device, the another device is also located at the right hand of the user.

Figure 8:
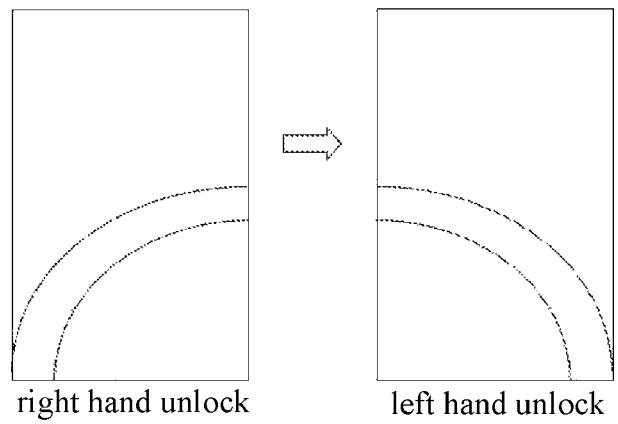
FIG. 8 is an example schematic diagram of a left hand mode and a right hand mode of a smartphone according to an example embodiment of this application.

In addition, the other device may also perform a corresponding operation, such as mode switching, according to the part where the other device is located. For example, as shown in FIG. 8, in response to that a smartphone is transferred from the right hand to the left hand, the smartphone FIG. may be automatically switched from the right hand mode at the left side of FIG. 8 to the left hand mode at the right side of FIG. 8, to facilitate an unlock operation of the user.

In addition, an embodiment of this application further provides a computer readable medium, comprising computer readable instructions for performing the following operations when being executed: executing operations of steps S120-S170 in the methods in the example embodiments shown in FIG. 1, FIG. 5, FIG. 6 and FIG. 7.

To sum up, the method of this application can implement identification of left and right limbs automatically, can perform a corresponding operation such as mode switching, user prompting, or device matching according to the identification result, and can assist another device in implementing the identification of the left and right limbs, thereby effectively simplifying device configuration steps, saving user time, and improving user experience.

Figure 9:
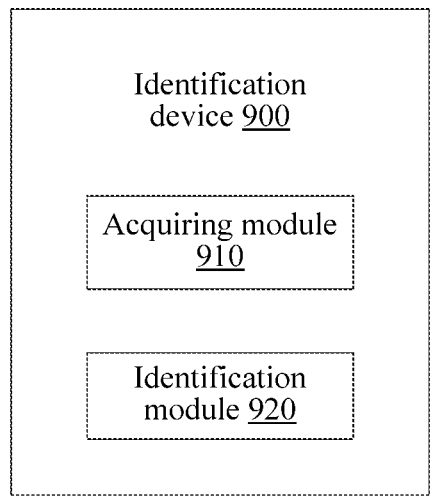
FIG. 9 is an example schematic structural diagram of modules of an identification device according to an example embodiment of this application.

FIG. 9 is a schematic structural diagram of modules of an identification device according to an embodiment of this application, and the identification device may be a smart wearable device such as a smart wrist band, a smart watch, or a smart arm band.

The identification device 900 may comprise:

an acquiring module 910, configured to acquire a first heartbeat propagation signal and a second heartbeat propagation signal separately from a target limb of a body; and an identification module 920, configured to identify whether the target limb is a left limb or a right limb at least according to the first heartbeat propagation signal and the second heartbeat propagation signal.

The identification device according to the embodiment of this application acquires the first heartbeat propagation signal and the second heartbeat propagation signal from the target limb, and identifies whether the target limb is a left limb or a right limb at least according to the first heartbeat propagation signal and the second heartbeat propagation signal, thereby implementing automatic identification of left and right limbs, simplifying configuration steps, and improving user experience.

Functions of the acquiring module 910 and the identification module 920 are described below in detail with reference to example embodiments.

Figure 10:
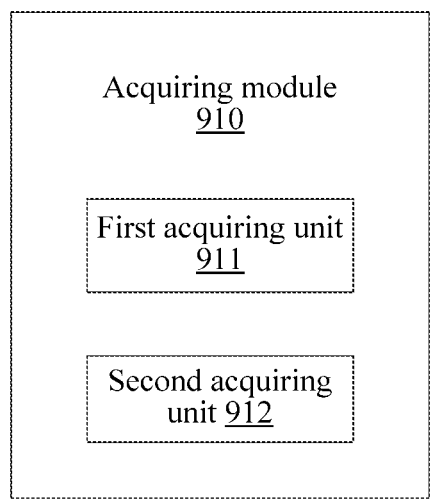
FIG. 10 is an example schematic structural diagram of modules of an acquiring module according to an example embodiment of this application.

Referring to FIG. 10, the acquiring module 910 may comprise:

a first acquiring unit 911, configured to acquire the first heartbeat propagation signal from the target limb of the body; and a second acquiring unit 912, configured to acquire the second heartbeat propagation signal from the target limb of the body, the second heartbeat propagation signal and the first heartbeat propagation signal being of different types.

The target limb is one of a left limb and a right limb, which may be a hand, an arm, a shoulder, a foot, or a leg. In addition, the identification of the target limb in this application comprises: identifying the left hand or right hand from two hands of a human body, identifying the left arm or right arm from two arms of a human body, identifying the left shoulder or right shoulder from two shoulders of a human body, identifying the left foot or right foot from two feet of a human body, or identifying the left leg or right leg from two legs of a human body. A person skilled in the art should understand that identification principles for hands, arms, shoulders, feet or legs are the same, and identification processes for hands, arms, shoulders, feet or legs are similar; therefore, for the sake of simplicity, this application emphasizes identifying the left hand or right hand from two hands of the human body.

The first heartbeat propagation signal and the second heartbeat propagation signal are heartbeat propagation signals of different types, in other words, the first heartbeat propagation signal and the second heartbeat propagation signal are two heartbeat propagation signals having different propagation speeds in the human body. For example, the first heartbeat propagation signal may be one of an electrocardiographic waveform signal and a blood flow pulsation waveform signal, and the second heartbeat propagation signal may be one of the electrocardiographic waveform signal and the blood flow pulsation waveform signal different from the first heartbeat propagation signal. The electrocardiographic waveform signal is a signal reflecting electrical activities generated by the heart during every cardiac cycle, and may be, for example, an electrocardiogram of the human body, which may be obtained by using, for example, a group of ECG detecting motor. The blood flow pulsation waveform signal is a signal reflecting blood flow pulsation generated by the heart during every cardiac cycle, which may be, for example, a photoplethysmography (PPG) pulse wave of the human body, which may be obtained by using, for example, an optical sensor, an ultrasonic sensor, an electromagnetic field sensor, or the like.

Figure 11:
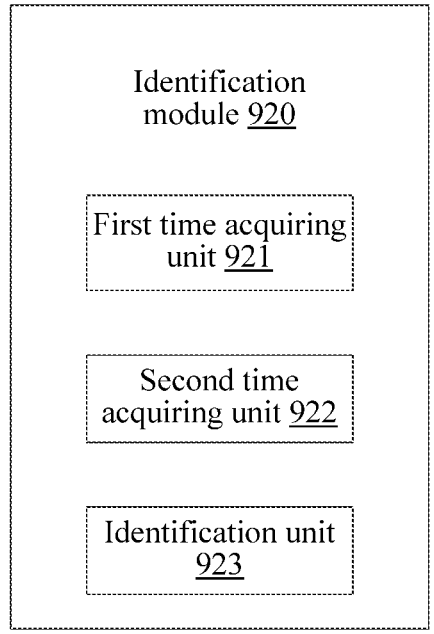
FIG. 11 is an example schematic structural diagram of modules of an identification module according to an example embodiment of this application.

Referring to FIG. 11, the identification module 920 may comprise:

a first time acquiring unit 921, configured to acquire a time corresponding to a first feature point on the first heartbeat propagation signal;

a second time acquiring unit 922, configured to acquire a time corresponding to a second feature point on the second heartbeat propagation signal, the second feature point being corresponding to the first feature point; and an identification unit 923, configured to identify whether the target limb is a left limb or a right limb at least according to a time difference between the time corresponding to the first feature point and the time corresponding to the second feature point.

The first feature point may be a crest on the first heartbeat propagation signal, and correspondingly the second feature point may be a crest on the second heartbeat propagation signal. Certainly, a person skilled in the art should understand that the first feature point may further be a trough on the first heartbeat propagation signal, and correspondingly, the second feature point may further be a trough on the second heartbeat propagation signal; or, the first feature point may further be a crest on the first heartbeat propagation signal, and correspondingly, the second feature point may further be a trough on the second heartbeat propagation signal; or the first feature point may further be a trough on the first heartbeat propagation signal, and correspondingly, the second feature point may further be a crest on the second heartbeat propagation signal. For the sake of simplicity, description is made below only by using an example in which the first feature point and the second feature point are respectively crests on corresponding heartbeat propagation signals.

Figure 12:
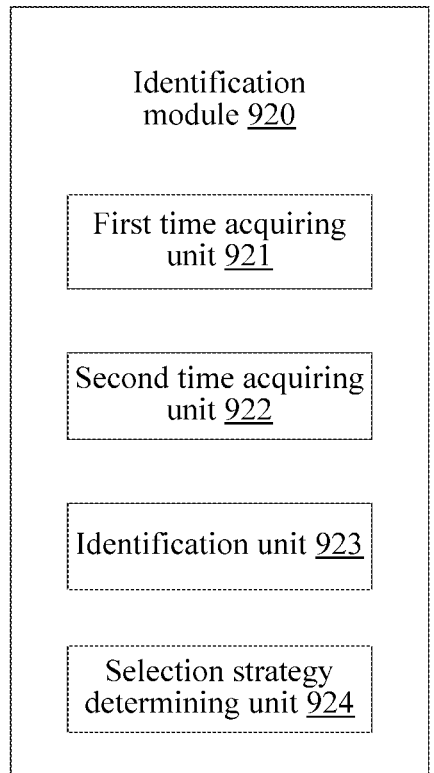
FIG. 12 is an example schematic structural diagram of modules of an identification module according to another example embodiment of this application.

Referring to FIG. 12, the identification module 920 may further comprise:

a selection strategy determining unit 924, configured to determine a strategy of selecting the first feature point and the second feature point according to a propagation speed relationship between the first heartbeat propagation signal and the second heartbeat propagation signal. For example, generally, the electrocardiographic waveform signal having a high propagation speed may be used as the first heartbeat propagation signal, and the blood flow pulsation waveform signal having a low propagation speed may be used as the second heartbeat propagation signal; in this way, a crest may be selected randomly on the electrocardiographic waveform signal to serve as the first feature point, and correspondingly, an $n^{th}$ crest after the first feature point may be selected on the blood flow pulsation waveform signal to serve as the second feature point, where n is a preset value. The preset value may be set in advance, for example, may be 1, 2, or the like. Meanwhile, in consideration of reducing the error, the first feature point and the second feature point are preferably located in a same cardiac cycle, that is, the preset value is 1.

Figure 13:
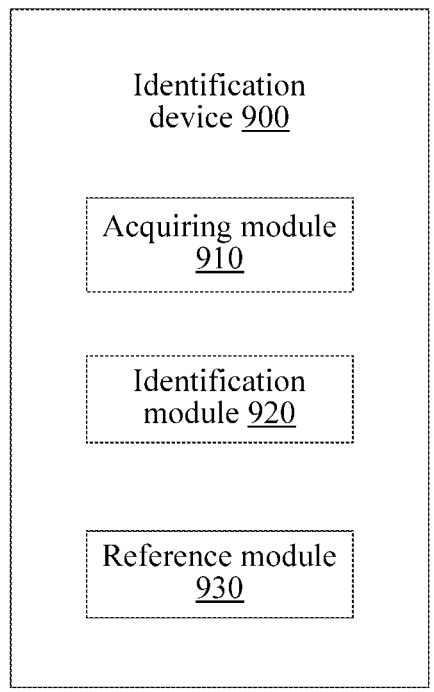
FIG. 13 is an example schematic structural diagram of modules of an identification device according to an example embodiment of this application.

In an example embodiment, referring to FIG. 13, the device 900 further comprises:

a reference module 930, configured to determine the reference time difference in advance.

Moreover, the identification unit 923 may be configured to identify whether the target limb is a left limb or a right limb according to a reference time difference and a time difference between the time corresponding to the first feature point and the time corresponding to the second feature point. For the specific identification process, reference may be made to the method embodiment in the foregoing, which is not repeated herein.

Figure 14:
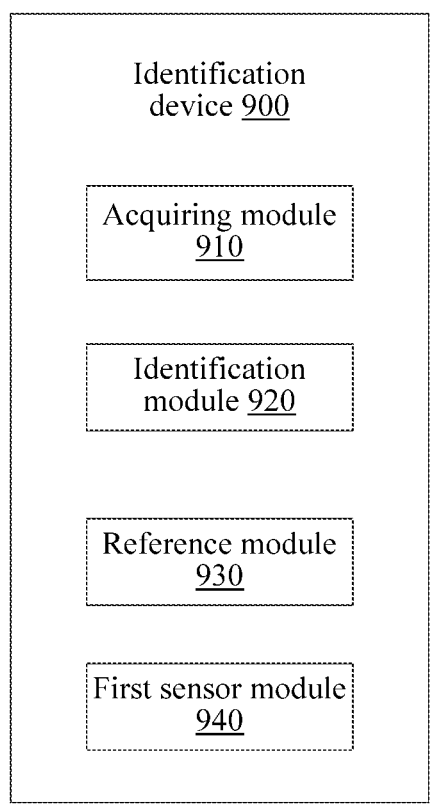
FIG. 14 is an example schematic structural diagram of modules of an identification device according to another example embodiment of this application.

In another example embodiment, to improve the identification precision, referring to FIG. 14, the device 900 further comprises:

a reference module 930, configured to determine the reference time difference in advance; and a first sensor module 940, configured to acquire first sensor information.

Moreover, the identification unit 923 is configured to identify whether the target limb is a left limb or a right limb according to a reference time difference, the first sensor information, and a time difference between the time corresponding to the first feature point and the time corresponding to the second feature point. For the specific identification process, reference may be made to the method embodiment in the foregoing, which is not repeated herein.

Figure 15:
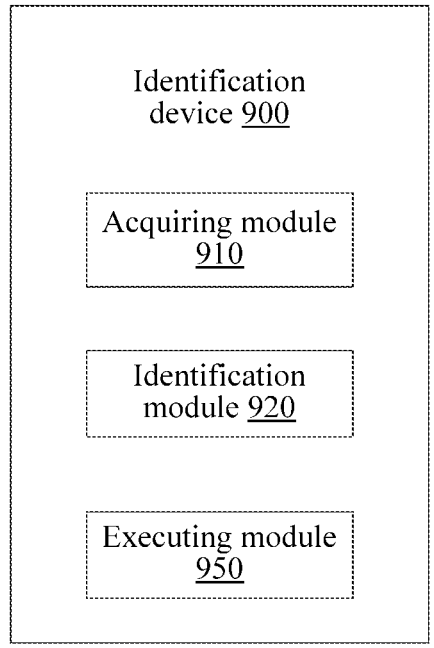
FIG. 15 is an example schematic structural diagram of modules of an identification device according to another example embodiment of this application.

Referring to FIG. 15, in an example embodiment, the device 900 further comprises:

an executing module 950, configured to execute a corresponding operation according to an identification result. The executing a corresponding operation may comprise: at least one of mode switching, user prompting, and device matching.

Figure 16:
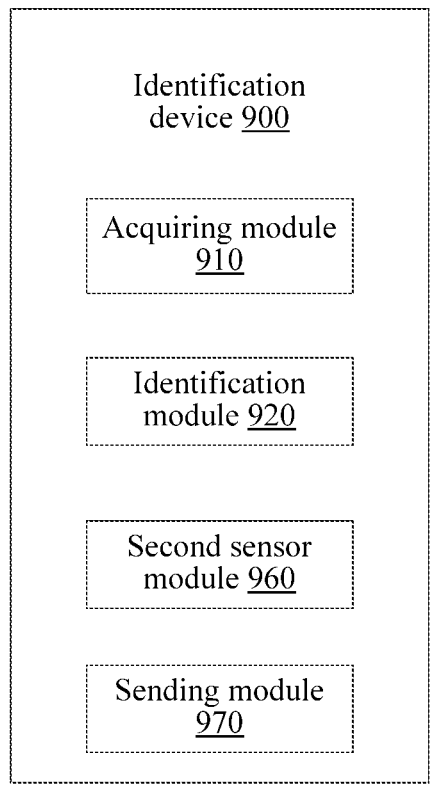
FIG. 16 is an example schematic structural diagram of modules of an identification device according to another example embodiment of this application.

Referring to FIG. 16, in another example embodiment, the device 900 further comprises:

a second sensor module 960, configured to acquire second sensor information; and a sending module 970, configured to send the identification result and the second sensor information to another device.

The second sensor information may comprise acceleration information, angle information, and the like. In addition, the other device may compare the second sensor information with sensor information of the other device, and may determine, according to a comparison result, a part of the body of the user where the other device is located. In addition, the other device may also perform a corresponding operation, such as mode switching, according to the part where the other device is located.

To sum up, the identification device of this application can implement identification of left and right limbs automatically, can perform a corresponding operation such as mode switching, user prompting, or device matching according to the identification result, and can assist another device in implementing the identification of the left and right limbs, thereby effectively simplifying device configuration steps, saving user time, and improving user experience.

Figure 17:
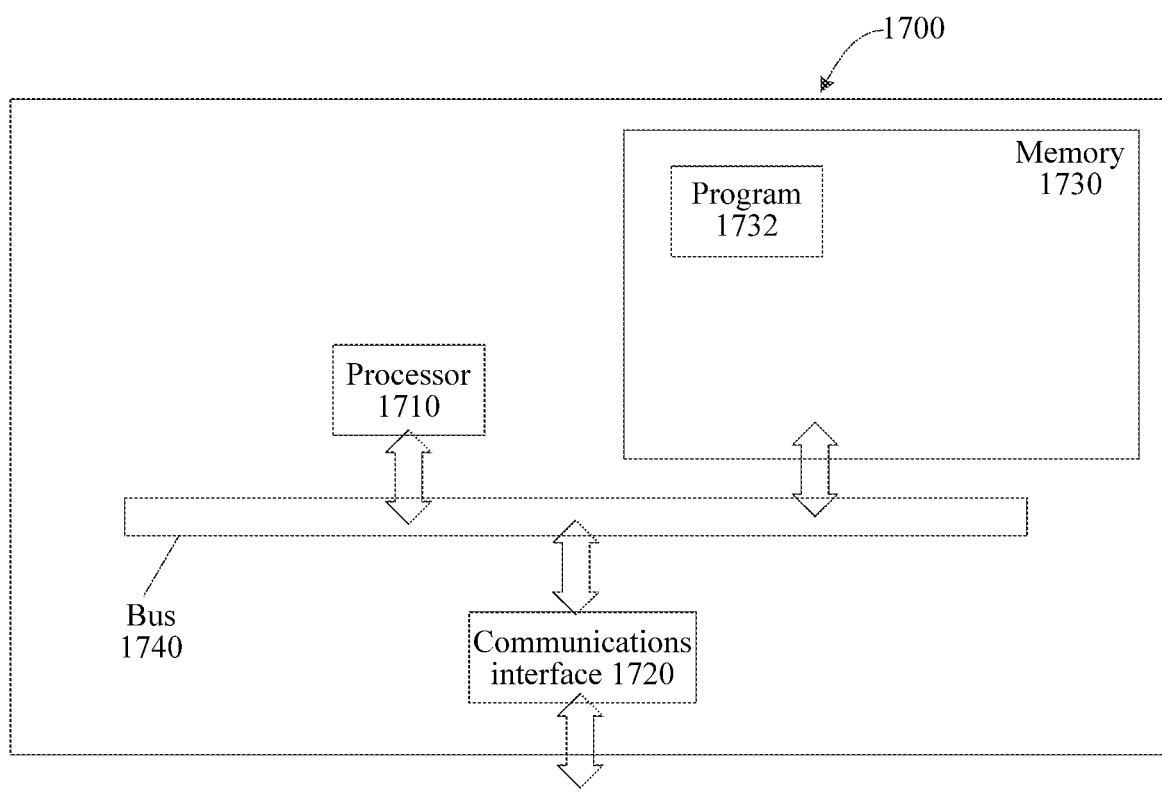
FIG. 17 is an example schematic diagram of a hardware structure of an identification device according to an embodiment of this application.

FIG. 17 shows a hardware structure of an identification device according to an embodiment of this application. The specific implementation of the identification device is not limited in the specific embodiments of this application, and referring to FIG. 17, the identification device 1700 may comprise:

a processor 1710, a communications interface 1720, a memory 1730, and a communications bus 1740.

The processor 1710, the communications interface 1720, and the memory 1730 complete mutual communications via the communications bus 1740.

The communications interface 1720 is configured to communicate with another network element.

The processor 1710 is configured to execute a program 1732, and specifically, can execute related steps in the method embodiment shown in FIG. 1.

Specifically, the program 1732 may comprise program code, the program code comprising a computer operation instruction.

The processor 1710 may be a central processing unit (CPU), or an application specific integrated circuit (ASIC), or be one or more integrated circuits configured to implement the embodiments of this application.

The memory 1730 is configured to store the program 1732. The memory 1730 may comprise a high-speed RAM memory, and may also comprise a non-volatile memory, for example, at least one magnetic disk memory. The program 1732 may specifically perform the following steps:

acquiring a first heartbeat propagation signal and a second heartbeat propagation signal separately from a target limb of a body; and identifying whether the target limb is a left limb or a right limb at least according to the first heartbeat propagation signal and the second heartbeat propagation signal.

For specific implementation of steps in the program 1732, reference may be made to related steps or modules in the foregoing embodiment, which is not described here. It can be clearly understood by persons skilled in the art that, for the purpose of convenient and brief description, as for a specific working process of the foregoing device and module, reference can be made to the corresponding process in the foregoing method embodiments, and the details are not described herein again.

A person of ordinary skill in the art may be aware that, in combination with the examples described in the embodiments disclosed in this specification, units and method steps may be implemented by electronic hardware, or a combination of computer software and electronic hardware. Whether the functions are performed by hardware or software depends on particular applications and design constraint conditions of the technical solutions. A person skilled in the art may use different methods to implement the described functions for each particular application, but it should not be considered that the implementation goes beyond the scope of this application.

When the functions are implemented in a form of a software functional unit and sold or used as an independent product, the functions may be stored in a computer-readable storage medium. Based on such an understanding, the technical solutions of this application essentially, or the part contributing to the prior art, or part of the technical solutions may be implemented in the form of a software product. The computer software product is stored in a storage medium, and includes several instructions for instructing a computer device (which may be a personal computer, a controller, a network device, and the like) to perform all or a part of the steps of the method described in the embodiment of this application. The foregoing storage medium includes: any medium that can store program codes, such as a USB flash disk, a removable hard disk, a read-only memory (ROM, Read-Only Memory), a random access memory (RAM, Random Access Memory), a magnetic disk, or an optical disk.

The foregoing example embodiments are merely intended for describing this application rather than limiting this application. A person of ordinary skill in the art should understand that modifications and variations may still be made without departing from the spirit and scope of this application. Therefore, all equivalent technical solutions shall fall within the scope of this application, and the patent protection scope of this application shall be subject to the claims.

What is claimed is:

1. A method, comprising:
   acquiring, by a device comprising a processor, a first heartbeat propagation signal and a second heartbeat propagation signal separately from a target limb of a body;
   acquiring a first time corresponding to a first feature point on the first heartbeat propagation signal;
   acquiring a second time corresponding to a second feature point on the second heartbeat propagation signal, the second feature point corresponding to the first feature point;
   identifying whether the target limb is a left limb or a right limb at least based on a comparison of a time difference between the first time and the second time to a reference time difference, wherein the reference time difference comprises a left-hand reference time difference and a right-hand reference time difference; and
   executing a corresponding operation according to an identification of the target limb, wherein the corresponding operation comprises at least one of mode switching, user prompting, or device matching.

2. The method of claim 1, wherein the first heartbeat propagation signal and the second heartbeat propagation signal are heartbeat propagation signals of different types.

3. The method of claim 1, wherein the first heartbeat propagation signal is one of an electrocardiographic waveform signal or a blood flow pulsation waveform signal, and the second heartbeat propagation signal is one of the electrocardiographic waveform signal or the blood flow pulsation waveform signal different from the first heartbeat propagation signal.

4. The method of claim 1, further comprising:
determining a strategy of selecting the first feature point and the second feature point according to a propagation speed relationship between the first heartbeat propagation signal and the second heartbeat propagation signal.

5. The method of claim 1, wherein the first feature point and the second feature point are located in a same cardiac cycle.

6. The method of claim 1, wherein the first feature point is a crest on the first heartbeat propagation signal, and the second feature point is a crest on the second heartbeat propagation signal.

7. The method of claim 1, further comprising:
acquiring first sensor information.

8. The method of claim 7, wherein the identifying whether the target limb is the left limb or the right limb comprises:
identifying whether the target limb is the left limb or the right limb based on the reference time difference, the first sensor information, and the time difference.

9. The method of claim 7, wherein the first sensor information comprises: at least one of pulse information, blood pressure information, body temperature information, motion state information, or body gesture information.

10. The method of claim 1, further comprising:
determining the reference time difference in advance.

11. The method of claim 1, further comprising:
acquiring second sensor information; and
sending the identification result and the second sensor information to another device.

12. The method of claim 1, wherein the target limb comprises: a hand, an arm, a shoulder, a foot, or a leg.

13. A device, comprising:
a memory that stores executable modules; and
a processor, coupled to the memory, that executes or facilitates execution of the executable modules, comprising:
an acquiring module configured to acquire a first heartbeat propagation signal and a second heartbeat propagation signal separately from a target limb of a body; and
an identification module configured for:
acquiring a first time corresponding to a first feature point on the first heartbeat propagation signal,
acquiring a second time corresponding to a second feature point on the second heartbeat propagation signal, the second feature point corresponding to the first feature point,
identifying whether the target limb is a left limb or a right limb at least based on a comparison of a time difference between the first time and the second time to a reference time difference, wherein the reference time difference comprises a left-hand reference time difference and a right-hand reference time difference; and
an executing module configured to execute a corresponding operation according to an identification of the target limb, wherein the corresponding operation comprises at least one of mode switching, user prompting, or device matching.

14. The device of claim 13, wherein the acquiring module comprises:

a first acquiring unit configured to acquire the first heartbeat propagation signal from the target limb of the body; and
a second acquiring unit configured to acquire the second heartbeat propagation signal from the target limb of the body, the second heartbeat propagation signal and the first heartbeat propagation signal being of different types.

15. The device of claim 13, wherein the identification module further comprises:
a selection strategy determining unit configured to determine a strategy of selecting the first feature point and the second feature point according to a propagation speed relationship between the first heartbeat propagation signal and the second heartbeat propagation signal.

16. The device of claim 13, wherein the executable modules further comprise:
a first sensor module configured to acquire first sensor information.

17. The device of claim 16, wherein the identification module is further configured to identify whether the target limb is the left limb or the right limb based on the reference time difference, the first sensor information, and the time difference.

18. The device of claim 13, wherein the executable modules further comprise:
a reference module configured to determine the reference time difference in advance.

19. The device of claim 13, wherein the executable modules further comprise:
a second sensor module configured to acquire second sensor information; and
a sending module configured to send the identification result and the second sensor information to another device.

20. The device of claim 13, wherein the device is a wearable device.

21. A computer readable storage device, comprising at least one executable instruction, which, in response to execution, causes a device comprising a processor to perform operations, comprising:
receiving a first heartbeat propagation signal and a second heartbeat propagation signal from a target limb of a body;
acquiring a first time corresponding to a first feature point on the first heartbeat propagation signal;
acquiring a second time corresponding to a second feature point on the second heartbeat propagation signal, the second feature point corresponding to the first feature point; and
identifying whether the target limb is a left limb or a right limb at least based on a comparison of a time difference between the first time and the second time to a reference time difference, wherein the reference time difference comprises a left-hand reference time difference and a right-hand reference time difference; and
executing a corresponding operation according to an identification of the target limb, wherein the corresponding operation comprises at least one of mode switching, user prompting, or device matching.

22. A device, characterized by comprising a processor and a memory, the memory storing executable instructions, the processor being connected to the memory via a communication bus, and when the identification device operates, the processor executes the executable instructions stored in the memory, so that the identification device executes operations, comprising:

measuring a first heartbeat propagation signal and a second heartbeat propagation signal from a target limb of a body;

obtaining a first time corresponding to a first feature point on the first heartbeat propagation signal;

obtaining a second time corresponding to a second feature point on the second heartbeat propagation signal, the second feature point corresponding to the first feature point; and identifying whether the target limb is a left limb or a right limb at least based on a comparison of a time difference between the first time and the second time to a reference time difference, wherein the reference time difference comprises a left-hand reference time difference and a right-hand reference time difference; and executing a corresponding operation according to an identification of the target limb, wherein the corresponding operation comprises at least one of mode switching, user prompting, or device matching.

23. The computer readable storage device of claim 21, wherein the first heartbeat propagation signal and the second heartbeat propagation signal are heartbeat propagation signals of different types.

24. The device of claim 22, wherein the first heartbeat propagation signal is one of an electrocardiographic waveform signal or a blood flow pulsation waveform signal, and the second heartbeat propagation signal is one of the electrocardiographic waveform signal or the blood flow pulsation waveform signal different from the first heartbeat propagation signal.

25. The device of claim 22, wherein the operations further comprise:

determining a strategy of selecting the first feature point and the second feature point according to a propagation speed relationship between the first heartbeat propagation signal and the second heartbeat propagation signal.

26. The device of claim 22, wherein the first feature point and the second feature point are located in a same cardiac cycle.

27. The computer readable storage device of claim 21, wherein the first heartbeat propagation signal is one of an electrocardiographic waveform signal or a blood flow pulsation waveform signal, and the second heartbeat propagation signal is one of the electrocardiographic waveform signal or the blood flow pulsation waveform signal different from the first heartbeat propagation signal.

28. The computer readable storage device of claim 21, wherein the operations further comprise:

determining a strategy of selecting the first feature point and the second feature point according to a propagation speed relationship between the first heartbeat propagation signal and the second heartbeat propagation signal.

29. The computer readable storage device of claim 21, wherein the first feature point and the second feature point are located in a same cardiac cycle.

* * * * *